United States Patent
Eganhouse

Patent Number: 5,678,991
Date of Patent: Oct. 21, 1997

[54] ORTHODONTIC APPLIANCE FOR THE CORRECTION OF CLASS III SKELETAL AND/OR DENTAL DEVIATIONS

[76] Inventor: Gerald R. Eganhouse, 295 30th St. SE., Cedar Rapids, Iowa 52403

[21] Appl. No.: 643,933

[22] Filed: May 7, 1996

[51] Int. Cl.$^6$ ................................................. A61C 3/00
[52] U.S. Cl. ................................................. 433/19
[58] Field of Search ................................. 433/19

[56] References Cited

U.S. PATENT DOCUMENTS

| | | | |
|---|---|---|---|
| 4,472,138 | 9/1984 | Howe | 433/19 |
| 4,871,310 | 10/1989 | Vardimon | 433/19 |
| 4,969,822 | 11/1990 | Summer | 433/19 |
| 5,324,196 | 6/1994 | Magill | 433/19 |

OTHER PUBLICATIONS

Balters, W.: Krafteinwirkung oder formgestaltende Reiszetzung? Zahnarztl. Welt 7:437–441, 1952.

Balters, W.: Reflexmechjanismus und Funktionablauf. Fortschr. Kieferorthop. 16:325–327, 1955.

Frankel, R.: Maxillary retrusion in CIII and treatement with the function corrector III. Trans Eur Orthodontic Soc 1970, pp. 249–259.

Major, Paul and ElBadrawy, H.E.: Maxillary protraction for early orthopedic correction of skeletal Class III malcclusion. Pediatric Dentistry: May/Jun., 1993—vol. 15, No. 3, pp. 203–207.

Major, Paul and Glover, Kenneth: Treatment of anterior cross-bites in the early mixed dentition. Journal of Canadian Dental Association: Jul. 1992, vol. 58 No. 7, pp. 574–579.

McNamara, James A., Jr.: An Orthopedic Approach to the Treatement of Class III Malcclusion in Young Patients. Journal of Clinical Orthodontics: Sep. 1987, vol. XXI, No. 9, pp.598–608.

Stensland, A., Wisth, P.J. and Boe, O.E.: Dentofacial changes in children with negative overjet treated by a combined orthodontic and orthopaedic approach. European Journal of Orthodontics 10 (1988) pp. 39–51.

Hickman, John: Maxillary Protraction Therapy: Diagnosis and Treatment. Journal of Clinical Orthodontics. Feb. 1991, vol. XXV, No. 2, pp. 102–113.

*Primary Examiner*—John J. Wilson
*Attorney, Agent, or Firm*—James C. Nemmers

[57] ABSTRACT

A two-piece orthodontic appliance used in the treatment of Class III malocclusions. The appliance consists of a maxillary part and a mandibular part each fitted to the patient's teeth and having smooth surfaces that engage each other when in the patient's mouth. The maxillary part covers the palate and has a protruding guide on its inferior surface that extends distally toward the palate. The mandibular part has a groove corresponding to the guide on the upper part so that the two parts are slidably engaged when in place in the patient's mouth. Elastics are combined with the two parts of the appliance to create an antagonistic force between the two parts, which then simultaneously apply an anterior force to the maxilla and a posterior force to the mandible. The appliance thus applies forces that work against Class III development growth vectors to correct or minimize their effect on the patient.

8 Claims, 2 Drawing Sheets

ORTHODONTIC APPLIANCE FOR THE CORRECTION OF CLASS III SKELETAL AND/OR DENTAL DEVIATIONS

BACKGROUND OF THE INVENTION

In the field of orthodontics, there are numerous skeletal and dental deviations that present a challenge to the orthodontist. One of these deviations that presents an especially difficult challenge is the treatment of Class III malocclusions. Classification of Class III growth conditions can be categorized in four different areas. These are:

1) Where the mandible has grown excessively in an anterior direction. This is a skeletal deviation.
2) Where the maxilla has failed to grow in an anterior direction adequately.

This is also a skeletal deviation.

3) Where a combination of 1) and 2) above exists in which both the maxillary and mandible deviate excessively at the same time, i.e. the maxillary has failed to grow anteriorly adequately while the mandible has grown excessively anteriorly.
4) Where a Class III malocclusion is due to a dentoalveolar malrelationship, in which case the teeth only will exhibit a Class III dental condition. This condition does not involve deviant skeletal growth.

Some of these conditions may require orthognathic surgery after growth has ceased. Certain cases can be treated without surgery using known appliances. For example, previous attempts have been made to apply correctional and/or antagonistic forces to the facial structures that exhibit these Class III conditions. Some of these attempts have used chin cup retraction devices. In appropriate cases, the use of facial masks and protraction headgear have been moderately successful. Lacking in previous methods was a method of disarticulating the arches in order to allow independent near-frictionless anterior-posterior movement. Moreover, any appliance has to be comfortable in order for compliance to be adequate.

There is therefore a need for an improved orthodontic appliance for use in correcting Class III conditions in the deciduous, preadolescent, or adolescent phases of growth. Any such appliance must be relatively simple, inexpensive and comfortable.

SUMMARY OF THE INVENTION

The device of the invention is a two-piece appliance designed to provide biological forces of equal magnitude to the mandible and the maxilla at the same time. The appliance of the invention will apply forces that work against Class III development growth vectors to correct or minimize their effect on the patient. The appliance is made of a hard, smooth material, such as acrylic, and consists of a maxillary (upper) part and a mandibular (lower) part. The maxillary part covers the palate and has a protruding guide extending distally toward the palate. The mandibular part has a groove corresponding to the guide on the upper part so that the two parts are slidably engaged when in place in the patient's mouth. Elastics are combined with the two parts of the appliance to create an antagonistic force between the two parts, which then simultaneously apply an anterior force to the maxilla and a posterior force to the mandible with equal magnitude. The flat sliding surfaces between the two parts of the appliance provide a near frictionless condition as the dentition is disoccluded during movement. This slide-type design also offers lateral as well as antero-posterior stability.

The appliance preferably is used in conjunction with a chin cup. An adaptable Class III mask may also be used with force application to the maxillary anterior-most hook of the appliance.

DESCRIPTION OF THE PREFERRED EMBODIMENT OF THE INVENTION

The timing of treatment in relation to dental and skeletal development has been extensively discussed in numerous scientific and professional publications. The authors generally agree that once diagnosed, treatment of Class III conditions should be commenced as early as possible and preferably in the late deciduous or early mixed dentition period. The ideal time to implement therapy using the appliance of the invention is when the maxillary and mandibular first permanent molars and permanent maxillary and mandibular central and lateral incisors are fully erupted in the Class III dentition. The appliance of the invention will now be described in detail.

Figure 8:
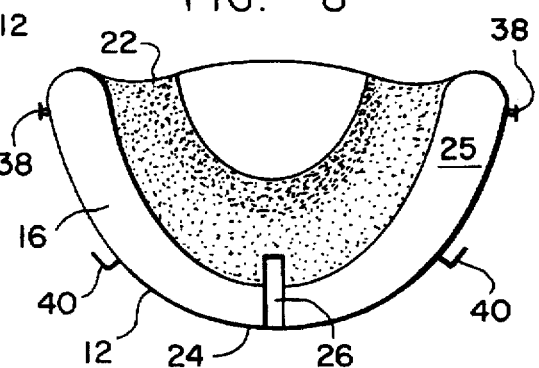
FIG. 8 is a plan view of the inferior surface of the maxillary part of the appliance.

The appliance 10 of the invention consists of two basic components, the maxillary (upper) part 12 and the mandibular (lower) part 14. The maxillary part 12 has a generally U-shaped portion 16 (FIG. 8) the superior surface 18 of which contains exact impressions of the crowns of the patient's upper teeth 20 so that the part 12 will fit exactly and comfortably when in the patient's mouth. As best seen in FIG. 8, the maxillary part 12 also has a palate portion 22 that covers the entire palate of the patient from the most posterior part of the dentition forward to allow correctional forces to be applied to the skeletal as well as the dental components of the maxilla. The maxillary part 12 will therefore cover the patient's palate and the crown areas and the entire lingual surface of the upper teeth 20 as well as the buccal and labial anterior aspects of the upper teeth 20, extending as far gingivally as possible (FIG. 2) while still allowing removal of the maxillary part 12 of the appliance 10 from the patient's mouth with light to moderate resistance. The U-shaped portion 16 of the maxillary part 12 has a smooth inferior surface 25 (FIG. 8) that is formed with a downwardly protruding guide 26. Guide 26 is rectangular in cross section and extends distally from the anterior surface 24 of the U-shaped portion 16 toward the palate portion 22 a sufficient distance to provide for lateral stability during progress of the correction. In a typical case, the length of the guide 26 will be in the range of 12-15 millimeters.

The mandibular part 14 (see FIG. 6) of the appliance 10 covers all the deciduous teeth as well as any erupted permanent teeth in the mixed dentition case. The mandibular part 14 therefore is generally U-shaped in configuration and is open in the interior so as not to interfere with the patient's tongue. As best seen in FIG. 3, similar to the superior surface 18 of the maxillary part 12, the inferior surface 28 of the mandibular part 14 contains exact impressions of the crowns of the patient's lower teeth 30 (FIGS. 3 and 4) so that the part 14 will fit exactly and comfortably when in the patient's mouth. Similar to the maxillary part 12 of the appliance 10, the mandibular part 14 extends inferiorly on the lingual, buccal and anterior aspects of the patient's lower teeth 30 while still allowing removal of the mandibular part 14 of the appliance 10 from the mouth with light to moderate resistance. The resistance to removal of both parts 12 and 14 of the appliance 10 should be manageable enough to allow the patient to remove and replace the two parts without frustration. If more anchorage is required in the mandibular anterior area, a horizontal 0.025 inch diameter stainless steel wire 32 (FIG. 9) can be incorporated on the mandibular part 14 extending downwardly from the inferior surface 28 so as to engage the labial aspects of the mandibular incisors near the height of the gingival margin to give added semi-rigid anchorage. (See FIGS. 2 and 3).

Figure 6:
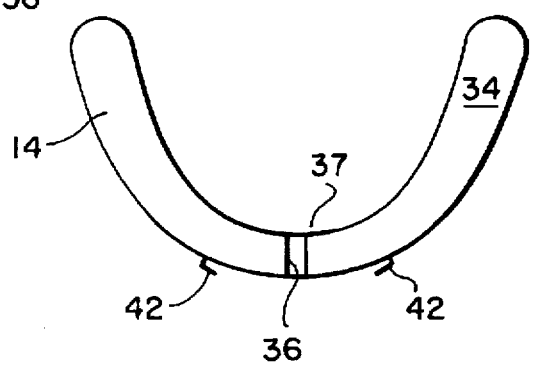
FIG. 6 is a plan view of the superior surface of the mandibular part of the appliance.

As best seen in FIG. 6, the mandibular part 14 has a smooth superior surface 34 that has formed centrally in it a rectangular groove 36 corresponding to the guide 26 of the maxillary part 12. Thus, groove 36 has the same cross-sectional shape as the guide 26 (FIG. 8). The groove 36 extends from the anterior-most part of the mandibular part 14 a distance of approximately 10 millimeters to the posterior-most part of the interior area 37 of the appliance. The inferior surface 25 of the maxillary part 12 and the superior surface 34 of the mandibular part 14 are flat and smooth so that when the two parts 12 and 14 are in contact, they will easily slide relative to each other, being directionally guided by movement of the guide 26 in the groove 36. When the appliance 10 is positioned in the mouth of the patient, the guide 26 and groove 36 allow for anterior-posterior slide as well as lateral stability as correction of the patient's condition progresses. No other known appliance affords this sliding action.

Figure 7:
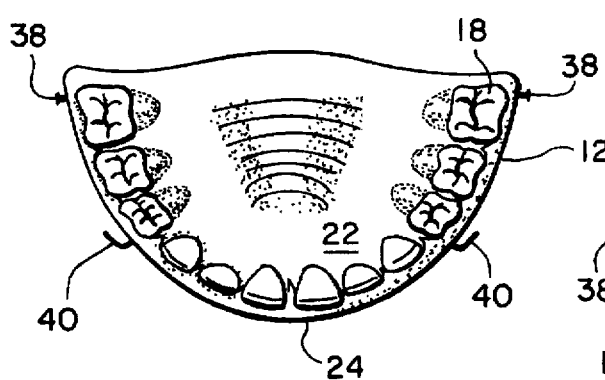
FIG. 7 is a plan view of the superior surface of the maxillary part of the appliance.
Figure 9:
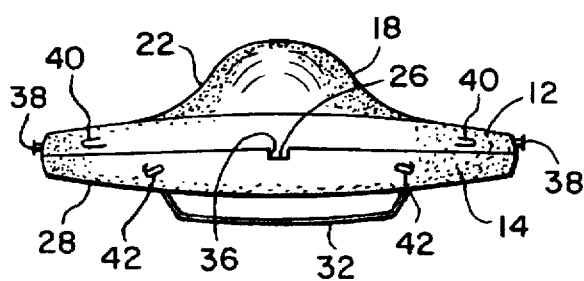
FIG. 9 is a frontal view of the appliance.

In order to provide for the application of forces along ideal vectors to achieve the antagonistic force between the two parts 12 and 14 of the appliance 10, elastics positioned as described hereinafter are attached to the maxillary part 12 and the mandibular part 14. The elastics are removably anchored on the parts 12 and 14 by the use of properly placed hooks. There are three hooks on each side of the appliance 10, two on the maxillary part 12 and one on the mandibular part 14. As best seen in FIGS. 7, 8 and 9, a first hook 38 is affixed to each side of the maxillary part 12 at a place so that the hook 38 will be positioned in the disto-buccal area of the maxillary permanent first molar when the appliance 10 is properly positioned in the mouth of the patient. A second hook 40 is affixed to each side of the maxillary part 12 at a place so that the hook 40 will be positioned in the first deciduous molar area. The third hook 42 is affixed to each side of the mandibular part 14 at a place so that the hook 42 will be positioned on each side in the area of the mandibular deciduous canine-permanent lateral incisor area. The hooks 38, 40 and 42 are made from stainless steel.

Figure 1:
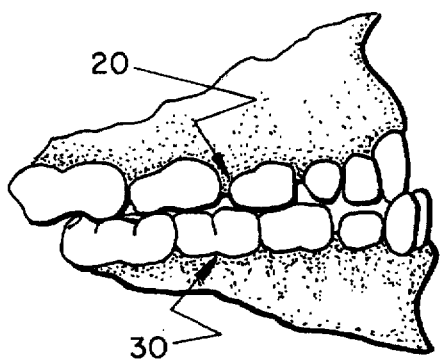
FIG. 1 is a profile view of the patient's mouth and illustrates a typical Class III condition in the early mixed dentition.
Figure 2:
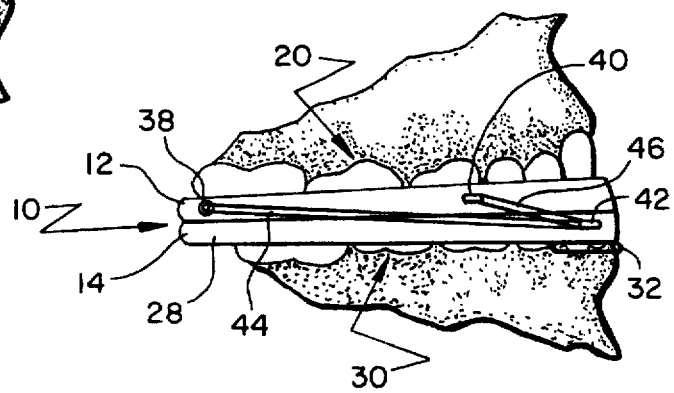
FIG. 2 is a view similar to FIG. 1 and shows the appliance of the invention in place at the beginning of treatment.
Figure 3:
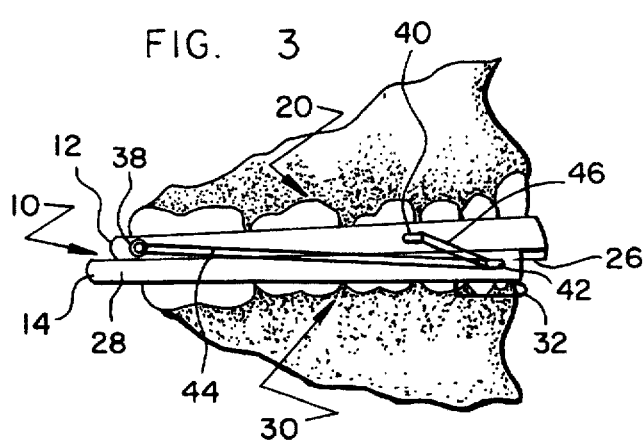
FIG. 3 is a view similar to FIG. 1 and shows the condition of the patient at the end of treatment with the appliance still in place.
Figure 4:
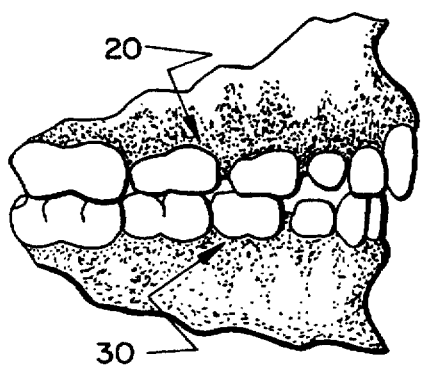
FIG. 4 is a view similar to FIG. 1 and shows the condition of the patient at the end of treatment with the appliance removed and illustrates an overjet of several millimeters.
Figure 5:
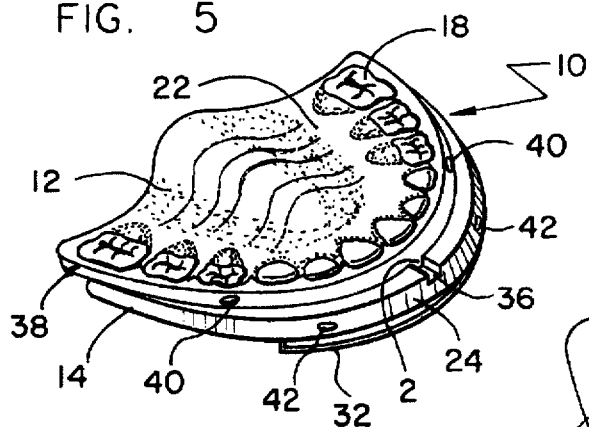
FIG. 5 is a perspective view of the appliance.

As illustrated in FIGS. 2 and 3, a first elastic 44 is removably attached between the first hook 38 on the maxillary part 12 and the third hook 42 on the mandibular part 14. A second elastic 46 is attached between the second hook 40 on the maxillary part 12 and the third hook 42 on the mandibular part 14. The first elastic 44 is longer than the second elastic 46 and applies a Class III force. The amount of the Class III force applied by elastic 44 can be varied by using one of the following standard sizes of elastics:

¼ inch 6 oz.
¼ inch 8 oz.
³⁄₁₆ inch 6 oz.
³⁄₁₆ inch 8 oz.

The size of the elastics 44 and 46 can be varied depending upon the comfort level of the patient. Elastic 46 provides both a Class III force and an inferior-superior force to keep the two parts 12 and 14 of the appliance 10 from separating from each other. The elastics 46 that apply a Class III force and an inferior-superior force on each side of the parts 12 and 14 are of one size only, a ⅛", 6 oz. size.

The design and construction of the appliance 10 will now be summarized in terms familiar to and understandable by persons skilled in the art. Alginate impressions of each dental arch are taken and poured in yellow or white stone to create models (not shown) of the parts 12 and 14 of the appliance 10. An occlusal wax bite registration is taken in centric relation. The models then are mounted on any standard articulator which allows opening and closing movements. However, the articulator must be of a design that has an adjustable incisal pin. No face bow transfer for model mounting is required. The models with wax bite registration are then mounted with the occlusal plane level in all directions and placed one half the distance inferiorly-superiorly between the bottom mounting plate and the top mounting plate of the articulator. Once the models are mounted in the articulator, the bite is opened 5-6 mm to allow sufficient thickness for construction of the appliance. If the wax bit is 5-6 mm in thickness, the bite need not be opened any farther. Once the models have been mounted, the maxillary part 12 and the mandibular part 14 can be formed from any suitable material such as heat cured acrylic with stainless steel hooks 38, 40 and 42 molded into the parts 12 and 14.

Figure 10:
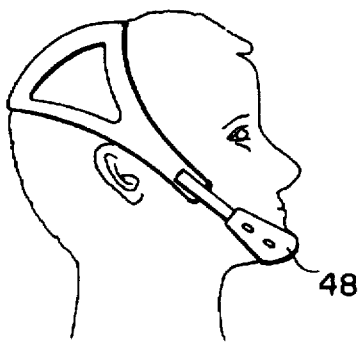
FIG. 10 is a lateral view of the patient's face and illustrates a chin cup in place.

After having made an appropriate diagnosis and having designed and constructed the appliance, the orthodontist will first insert the appliance 10 into the mouth of the patient and then apply the elastics 44 and 46. The anterior portions of both parts 12 and 14 will be flush with each other when the appliance is initially inserted. (See FIG. 2). The appliance 10 will free the malocclusion antero-posteriorly to allow the forces exerted by the elastics 44 and 46 to be controlled and directed so as to gradually correct the condition. The appliance 10 allows each dental arch to work against the other in a substantially frictionless method with all forces in a tolerable magnitude and in the correct direction. If the patient's tempero-mandibular joints become too tender during treatment, the force exerted by the long elastic 44 can be decreased to a comfortable level. Although it may take several days for the patient to adapt to the appliance, once adaptation has been made, the patient will feel surprisingly comfortable wearing the appliance. As the correction progresses, the maxillary part 12 of the appliance 10 will slide anteriorly relative to the mandibular part 14 giving a visual measure of the progress of the correction. (See FIG. 3). The appliance should be worn by the patient up to 12 hours per day, preferably at night, so that the chin cup 48 can be worn easily and in relative privacy. Depending upon the severity of the condition being corrected, treatment may take 15 to 24 months. The appliance preferably is used in conjunction with a commercially available chin cup 48 (see FIG. 10), such as the one supplied by GAC International, Inc., catalog designation SOF (Hi pull). An adaptable Class III mask (Dr. Henri Petit) marketed by Great Lakes Orthodontics Ltd., can also be used with force application to the maxillary anterior-most hooks 40.

Fabrication of the appliance of the invention is relatively simple and the cost of production is reasonable. The appliance is easy to use, relatively comfortable for the patient and can easily be removed and reinserted daily by the patient without assistance. If used without a chin cup or mask, the appliance has a definite esthetic advantage,

Having thus described the invention in connection with a preferred embodiment thereof, it will be evident to those skilled in the art that various revisions and modifications can be made to the preferred embodiment without departing from the spirit and scope of the invention. It is my intention, however, that all such revisions and modifications that are obvious to those skilled in the art will be included within the scope of the following claims.

What is claimed is as follows:

1. An orthodontic appliance for correcting Class III skeletal and/or dental deviations in a patient, said appliance comprising: a maxillary part having a generally U-shaped portion with a superior surface and an inferior surface, the superior surface of the U-shaped portion of the maxillary part containing impressions of the crowns of the patient's upper teeth, the maxillary part also having a palate portion for covering substantially all of the patient's palate from the most posterior part of the dentition forward, the inferior surface of the U-shaped portion of the maxillary part being substantially flat and smooth and having a centrally located guide protruding downwardly from the surface and extending distally from the anterior-most surface of the U-shaped portion toward the palate portion, a mandibular part having a superior surface and an inferior surface and being generally U-shaped with an open interior and with the inferior surface of the mandibular part containing impressions of the crowns of the patient's lower teeth, the superior surface of the mandibular part being substantially flat and smooth and having a centrally located groove corresponding to the guide of the maxillary part so that the guide will be engaged in the groove when the maxillary part and the mandilbular part are properly positioned in the patient's mouth, first hooks combined with the posterior portion of the maxillary part on each side, second hooks combined with the anterior portion of the maxillary part on each side, third hooks combined with the anterior portion of the mandibular part on each side forwardly of the second hook when the maxillary and mandibular parts are engaged, a first elastic member extending between each of the first and third hooks to apply a Class III force, and a second elastic member extending between the second and third hooks to apply both a Class III force and an inferior-superior force.

2. The orthodontic appliance of claim 1 in which the guide has a rectangular cross-sectional shape and the groove has a corresponding rectangular cross-sectional shape.

3. The orthodontic appliance of claim 2 in which the guide is of a length in the range of 12 to 15 millimeters.

4. The orthodontic appliance of claim 1 in which the anterior most portions of the maxillary part and the mandibular part are substantially flush when properly positioned in the patient's mouth at the start of the correction.

5. The orthodontic appliance of claim 1 in which a first hook is affixed to each side of the maxillary part so that each first hook will be positioned in the disto-buccal area of the patient's maxillary permanent first molar when the appliance is properly positioned in the patient's mouth.

6. The orthodontic appliance of claim 5 in which a second hook is affixed to each side of the maxillary part so that each second hook will be positioned in the area of the patient's first deciduous molar when the appliance is properly positioned in the patient's mouth.

7. The orthodontic appliance of claim 6 in which a third hook is affixed to each side of the mandibular part so that each third hook will be positioned in the area of the patient's mandibular deciduous canine-permanent lateral incisor when the appliance is properly positioned in the patient's mouth.

8. The orthodontic appliance of claims 1, 2, 3, 4, 5, 6 or 7 in which an anchor wire is affixed to the anterior portion of the mandibular part, the wire extending downwardly from the inferior surface of the mandibular part and laterally across the anterior portion of the mandibular part so as to engage the labial aspects of the patient's mandibular incisors near the height of the gingival margin when the appliance is properly positioned in the patient's mouth.

* * * * *